US009486173B2

(12) United States Patent
Fan et al.

(10) Patent No.: US 9,486,173 B2
(45) Date of Patent: Nov. 8, 2016

(54) SYSTEMS AND METHODS FOR ADJUSTABLE VIEW FREQUENCY COMPUTED TOMOGRAPHY IMAGING

(71) Applicant: General Electric Company, Schenectady, NY (US)

(72) Inventors: Jiahua Fan, New Berlin, WI (US); Jed Douglas Pack, Glenville, NY (US); Guangzhi Cao, Madison, WI (US); David Joseph Pitterle, Waukesha, WI (US); Grant Morey Stevens, Cedarburg, WI (US)

(73) Assignee: General Electric Company, Schenectady, NY (US)

( * ) Notice: Subject to any disclaimer, the term of this patent is extended or adjusted under 35 U.S.C. 154(b) by 228 days.

(21) Appl. No.: 14/451,616

(22) Filed: Aug. 5, 2014

(65) Prior Publication Data
US 2016/0038113 A1  Feb. 11, 2016

(51) Int. Cl.
*A61B 6/00* (2006.01)
*A61B 6/03* (2006.01)

(52) U.S. Cl.
CPC .............. *A61B 6/032* (2013.01); *A61B 6/037* (2013.01); *A61B 6/488* (2013.01); *A61B 6/542* (2013.01)

(58) Field of Classification Search
CPC .... A61B 6/5205; A61B 6/037; A61B 6/032; A61B 6/542; A61B 6/488
USPC .................................... 378/4–20, 95, 96, 97
See application file for complete search history.

(56) References Cited

U.S. PATENT DOCUMENTS

| | | |
|---|---|---|
| 5,400,387 A | 3/1995 | Gard |
| 5,485,494 A | 1/1996 | Williams |
| 5,558,638 A | 9/1996 | Evers |
| 5,625,662 A | 4/1997 | Toth |
| 5,696,807 A | 12/1997 | Hsieh |
| 5,822,393 A | 10/1998 | Popescu |
| 5,867,555 A * | 2/1999 | Popescu ................. A61B 6/032 378/16 |
| 6,094,468 A | 7/2000 | Wilting |
| 6,507,639 B1 | 1/2003 | Popescu |
| 6,744,846 B2 | 6/2004 | Popescu |
| 7,639,776 B2 | 12/2009 | Gohno |

* cited by examiner

*Primary Examiner* — Courtney Thomas
(74) *Attorney, Agent, or Firm* — Dean D. Small; The Small Patent Law Group, LLC.

(57) ABSTRACT

An imaging system includes a computed tomography (CT) acquisition unit and a processing unit. The CT acquisition unit includes an X-ray source and a CT detector configured to collect CT imaging data of an object to be imaged. The X-ray source and CT detector are configured to be rotated about the object to be imaged and to collect a series of views of the object as the X-ray source and CT detector rotate about the object to be imaged. The processing unit is operably coupled to the CT acquisition unit and configured to control the CT acquisition unit to vary a view duration for the views of the series. The view duration for a particular view defines an imaging information acquisition period for the particular view, wherein the series of views includes a first group of views having a first view duration and a second group of views having a second view duration that is different than the first view duration.

22 Claims, 7 Drawing Sheets

SYSTEMS AND METHODS FOR ADJUSTABLE VIEW FREQUENCY COMPUTED TOMOGRAPHY IMAGING

BACKGROUND OF THE INVENTION

The subject matter disclosed herein relates generally to systems and methods for computed tomography (CT) imaging.

In CT imaging, an X-ray source may be rotated around an object to obtain imaging information. X-rays from the source attenuated by the object may be collected or detected by a detector and used to reconstruct an image. Patient radiation dose from the X-ray source is a concern in clinical practice.

One approach to reducing radiation dose while attempting to maintain image quality is automatic exposure control (AEC). In AEC, an input radiation flux (or radiation provided by an X-ray source) is modulated during a scan to attempt to achieve a desired image quality based on pre-measurement of a patient. However, for large patients, for example, an imaging system may reach the limits of its capability, preventing the system from generating enough flux at various imaging angles, and the desired image quality may not be obtained. Low flux artifacts may be introduced in the images. Also, when using low dose scans and for certain types of measurements, photon starvation and electronic noise may dominate the measurements or otherwise adversely affect imaging.

BRIEF DESCRIPTION OF THE INVENTION

In one embodiment, an imaging system is provided that includes a computed tomography (CT) acquisition unit and a processing unit. The CT acquisition unit includes an X-ray source and a CT detector configured to collect CT imaging data of an object to be imaged. The X-ray source and CT detector are configured to be rotated about the object to be imaged and to collect a series of views of the object as the X-ray source and CT detector rotate about the object to be imaged. The processing unit is operably coupled to the CT acquisition unit and configured to control the CT acquisition unit to vary a view duration for the views of the series. The view duration for a particular view defines an imaging information acquisition period for the particular view, wherein the series of views includes a first group of views having a first view duration and a second group of views having a second view duration that is different than the first view duration. The view duration may be varied as a function of rotation angle or view angle. For example, the first group may correspond to a first range or ranges of rotational angles, and the second group may correspond to a different, second range or ranges of rotational angles.

In another embodiment, a method is provided that includes acquiring computed tomography (CT) imaging data of an object using a CT acquisition unit comprising an X-ray source and CT detector that rotate about the object. The CT imaging data is acquired in a series of views as the X-ray source and CT detector are rotated about the object. The method also includes controlling the CT acquisition unit, during CT imaging data acquisition, to vary a view duration for the views of the series. The view duration for a particular view defines an imaging information acquisition period for the particular view. The series of views includes a first group of views having a first view duration and a second group of views having a second view duration that is different than the first view duration. Further, the method includes reconstructing an image using the CT imaging data.

In another embodiment, a method is provided that includes acquiring a scout image of an object using a computed tomography (CT) acquisition unit comprising an X-ray source and CT detector. The method also includes determining, using at least one processing unit, based on the scout image, a scan configuration to be provided by the CT acquisition unit to achieve a desired IQ at a uniform view duration. Also, the method includes comparing the determined scan configuration to a capability of the CT acquisition unit. If the capability of the imaging system does not meet the determined scan configuration, a view duration of views of a series is varied during acquisition of CT imaging data to provide the desired IQ. The view duration for a particular view defines an imaging information acquisition period for the particular view. During acquisition of CT imaging data, the X-ray source and CT detector are rotated about the object, and the CT imaging data is acquired in the series of views as the X-ray source and CT detector are rotated about the object. The method also includes reconstructing an image using the CT imaging data.

DETAILED DESCRIPTION OF THE INVENTION

Figure 1:
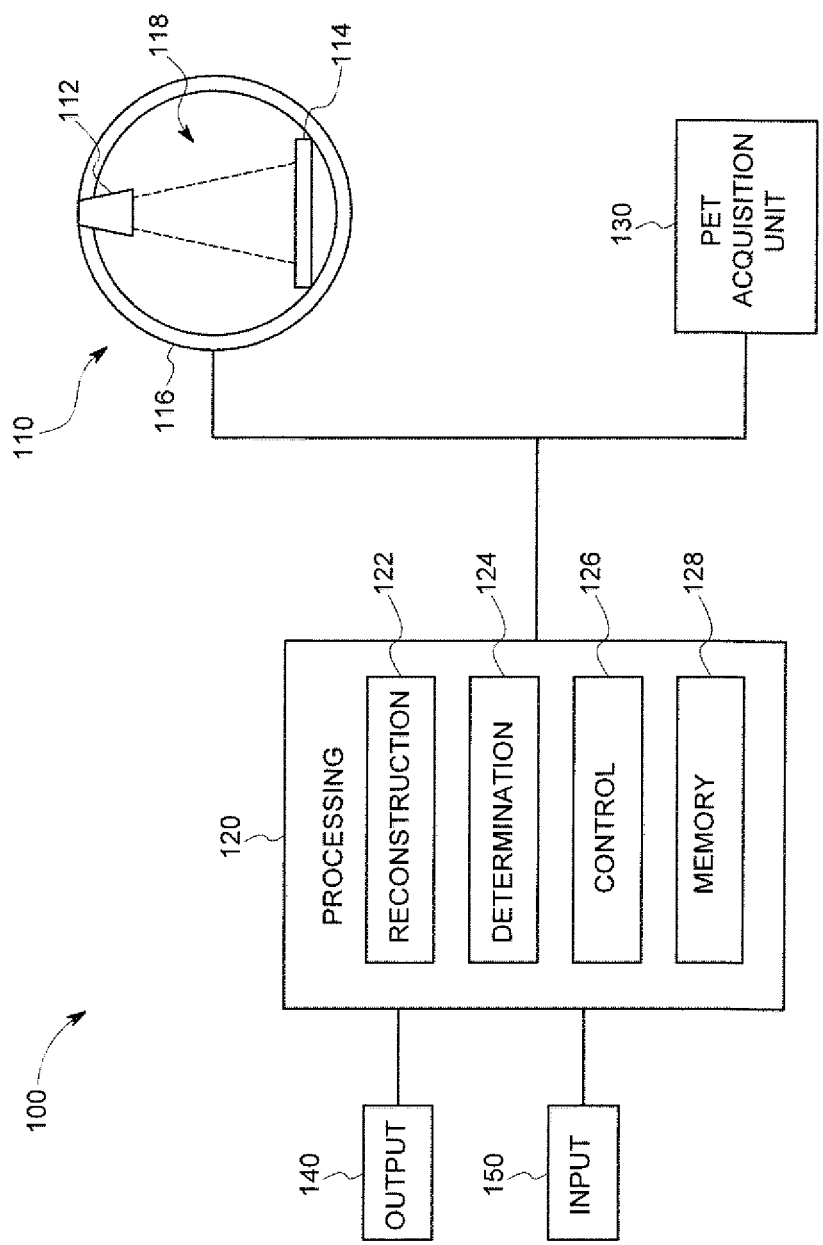
FIG. 1 is a schematic block diagram illustrating an imaging system in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for adjusting the duration (or period) or frequency of views used to collect computed tomography (CT) imaging information. As discussed herein, CT information may be collected by rotating an X-ray source and detector about an object to be imaged, and collecting CT information in a series of views. The series of views may be collected during the course of a single rotation, less than a rotation, or a number of rotations of a gantry to which the X-ray source and detector are mounted. The view duration for the individual views of the series, or length or period of imaging information collection for each view, may be controlled by triggering of a blanking period between adjacent views or acquisition periods. For example, in various embodiments, the view duration may be varied or adjusted as a function of rotational angle or view angle. The view duration for a particular view defines an imaging information acquisition period for that particular view. Views having a longer duration (or shorter frequency) will, for the same amount of radiation flux and attenuation, collect more information (or counts) than views having a shorter duration. By adjusting the view length or frequency, the amount of information collected (and image quality) may be adjusted without increasing an amount of radiation flux. For example, by using a longer view for portions or view angles of an object having greater attenuation, more information may be collected to help improve a signal to noise ratio (SNR). For regions of interest that are relatively small and positioned close to the iso-center of the imaging system, a relatively long view duration (or short view frequency) may be utilized without substantial reduction of image quality (e.g., due to blurring). By varying the view duration as the X-ray source and CT detector rotate about the object, an amount of flux collected (e.g., radiation that has passed through the object) may be adjusted, for example, based on object size and/or shape.

In various embodiments, the number of views sampled per rotation or view frequency may be adjusted automatically, for example, based on prior knowledge of the patient and/or clinical application. Such prior knowledge may include the size of the patient, attenuation of the patient (e.g., an attenuation determined using a scout scan), and knowledge of the clinical scenario and/or clinical tasks related to the scan. In some embodiments, with the system (e.g., gantry to which the X-ray source and detector are mounted) rotating about the object at a constant rotational speed, the number of views acquired is dynamically adjusted from rotation to rotation and/or within each rotation at different angles. Accordingly, the flux collected (or counts collected or imaging information collected) at each view (or group of views) may be adjusted, for example based on the corresponding object size/shape and/or target image quality (IQ) metrics. In some embodiments, the view adjustment may be integrated into an automatic exposure control (AEC) or other scheme that modulates the radiation flux provided by the X-ray source. Various embodiments help improve system capability for imaging a given patient at a desired diagnostic image quality.

An example of a clinical CT study in accordance with various embodiments will now be discussed. For clinical CT studies, typically a scout scan (or scans) may first be acquired. Using the scout scan (or scans), patient size and shape information are calculated. Based on one or more predetermined or prescribed IQ targets (e.g., noise index target), scan settings such as tube voltage (kVp), tube current (mA), and scan speed, among others, may be determined. However, for a large patient, and/or for low dose protocols, the system capability or ability to provide a desired dose may be met or exhausted before the desired image quality is reached. If the system's ability to provide a desired dose is reached, or a dose ceiling or limit is met, without the desired image quality being provided, the view duration or frequency may be adjusted to provide the desired capability or image quality. In some embodiments, the view duration or frequency may be adjusted within a single rotation. Additionally or alternatively, the view duration or frequency may be adjusted between rotations (e.g., rotations taking place at different portions along a length of an object to be imaged, such as a patient). The view duration adjustment may be based on the patient shape/size as well as the specific clinical application. For example, for larger patients, or those view angles corresponding to a thicker portion of a patient (or portion of a patient having a greater attenuation), a longer view duration (or smaller view frequency) may be employed. As another example, for objects or regions of interest that are more closely positioned to an iso-center of a system (e.g., the center of a bore about which the X-ray source and detector rotate), a longer view duration (or smaller view frequency) may be employed, as blurring is reduced for volumes closer to the iso-center. As another example, a CT system may be used in conjunction with a positron emission tomography (PET) or other nuclear medicine (NM) system for attenuation correction. Generally, lower resolution or image quality may be required for attenuation correction, such that a longer view duration may be utilized to allow for lowering of radiation flux used for attenuation correction.

One approach that may be used to determine a number of views per rotation may use the following: # of views per rotation=$((\pi*\text{DFOV})/\text{detector}_{pitchISO})* (\text{SID}/(\text{SID}-\text{DFOV}/2))$, where DFOV refers to the reconstruction field of view, $\text{detector}_{pitchISO}$ refers to the detector sampling distance at the iso-center, and SID is the source to iso-center distance. For example, a cardiac high-resolution mode of CT scanning may have a relatively fast scan speed. Due to the fast scan speed, for a large patient, it may be a challenge to provide an amount of radiation flux corresponding to a desired image quality. However, because the heart may be imaged within a relatively small field of view (e.g., 25 centimeters), a number of views needed based on the region of interest (e.g., the heart) may be determined, which may help alleviate the low signal/flux issues without changing or increasing the radiation dose. Again, as discussed herein, the number of views need not be uniform, but may be varied for different portions of a rotation (and/or from rotation to rotation). For example, as the clinical interest changes along the length of a patient, the # of views per rotation may be adjusted accordingly. As another example, the view duration may be adjusted to provide a longer view duration for view angles passing through thicker parts of an object and to provide a shorter view duration for view angles passing through thinner parts of an object.

Various embodiments provide improved imaging. A technical effect of at least one embodiment includes improved image quality without increasing radiation dose. A technical effect of at least one embodiment includes providing a desired image quality using a limited amount of radiation dose (e.g., radiation dose limited by a protocol, or radiation dose limited by a system capability). A technical effect of at least one embodiment includes adjustment of a view duration or frequency to provide improved numbers of counts or improved imaging information based on noise levels. A technical effect of at least one embodiment is to reduce noise in images.

FIG. 1 illustrates an imaging system 100 in accordance with an embodiment. The imaging system 100 may be configured, for example, to perform computed tomography (CT) scanning of an object, such as human or animal patient (or portion thereof). The imaging system 100 includes a computed tomography (CT) CT acquisition unit 110, a positron emission tomography (PET) acquisition unit 130, and a processing unit 120. The CT acquisition unit 110 and PET acquisition unit 130 are shown offset in FIG. 1 for ease of illustration; however, in practice the CT acquisition unit 110 and PET acquisition unit 130 may be aligned, for example, along a common bore. Generally, the CT acquisition unit 110 is configured to acquire projection data or imaging data (e.g., CT data or CT imaging information), and the processing unit 120 is configured to reconstruct images using the data acquired by the CT acquisition unit 110 and/or PET acquisition unit 130. It may be noted that various embodiments may include additional components, or may not include all of the components shown in FIG. 1 (for example, various embodiments may provide sub-systems for use with other sub-systems to provide an imaging system). As another example, the PET acquisition module 130 may not be included in various embodiments. In embodiments that include the PET acquisition module 130, information from the CT acquisition module 110 may be utilized by the processing unit 120 to perform attenuation correction for PET imaging data. Further, it may be noted that certain aspects of the imaging system 100 shown as separate blocks in FIG. 1 may be incorporated into a single physical entity, and/or aspects shown as a single block in FIG. 1 may be shared or divided among two or more physical entities.

The depicted CT acquisition unit 110 includes an X-ray source 112 and a CT detector 114. (For additional information regarding example CT systems, see FIG. 5 and related discussion herein; see also FIGS. 6-7 and related discussion for additional information regarding CT and PET systems.)

The X-ray source 112 and the CT detector 114 (along with associated components such as bowtie filters, source collimators, detector collimators, or the like (not shown in FIG. 1)) may rotate about a central axis of a bore of a gantry 116 of the system 100.

Generally, X-rays from the X-ray source 112 may be guided to an object to be imaged through a source collimator and bowtie filter. The object to be imaged, for example, may be a human patient, or a portion thereof (e.g., head or torso, among others). The source collimator may be configured to allow X-rays within a desired field of view (FOV) to pass through to the object to be imaged while blocking other X-rays. The bowtie filter module may be configured to absorb radiation from the X-ray source 112 to control distribution of X-rays passed to the object to be imaged.

X-rays that pass through the object to be imaged are attenuated by the object and received by the CT detector 114 (which may have a detector collimator associated therewith), which detects the attenuated X-rays and provides imaging information to the processing unit 120. The processing unit 120 may then reconstruct an image of the scanned portion of the object using the imaging information (or projection information) provided by the CT detector 114. The processing unit 120 may include or be operably coupled to the output unit 140, which in the illustrated embodiment is configured to display an image, for example, an image reconstructed by the processing unit 120 using imaging information from the CT detector 114. The depicted input unit 150 is configured to obtain input corresponding to a scan to be performed, with the processing unit 120 using the input to determine one or more scan settings (e.g., tube voltage, tube current, scanning rotation speed, number of axial slabs to be imaged, duration length for one or more groups of views, or the like). The input unit 150 may include a keyboard, mouse, touchscreen or the like to receive input from an operator, and/or may include a port or other connectivity device to receive input from a computer or other source.

In the illustrated embodiment, the X-ray source 112 is configured to rotate about the object. For example, the X-ray source 112 and the CT detector 114 may be positioned about a bore 118 of the gantry 116 and rotated about the object to be imaged. As the X-ray source 112 rotates about the object during an imaging scan, X-rays received by the CT detector 114 during one complete rotation provide a 360 degree view of X-rays that have passed through the object. Other scanning ranges may be used in alternative embodiments. (It may also be noted that an individual scout scan may be performed from a single orientation, or with the X-ray source 112 and CT detector 114 at a stationary position.) The CT imaging information may be collected as a series of views that together make up a rotation or portion thereof. Each view may have a view duration during which information (e.g., counts) is collected for the particular view. The view duration for a particular view defines an imaging information acquisition period for that particular view. The length of the view may be controlled by triggering a blanking interval for acquisition of information from the CT detector 114 which separates a first view from the next view in the series. As the length of the view is specified by a duration of time, the number of views or view frequency may be understood as being inversely proportional to the view duration. As discussed herein, the view duration (or number of views or view frequency) may be varied during CT imaging information acquisition within a given rotation and/or between different rotations.

As indicated herein, the processing unit 120 is configured to control various aspects of the acquisition units and/or to reconstruct an image using information obtained via the acquisition units. For example, the processing unit 120 may be configured to reconstruct a CT image using information collected by the CT acquisition unit 110. As another example, the processing unit 120 may be configured to reconstruct a PET image using information from the PET acquisition unit 130, and using information from the CT acquisition unit 110 for attenuation correction.

The depicted processing unit 120 is operably coupled to the input unit 150, the output unit 140, the CT acquisition unit 110, and the PET acquisition unit 130. The processing unit 120, for example, may receive information regarding a scan from the input unit 150 that may be utilized in determining scanning parameters to be used in acquiring CT imaging information. As another example, the processing unit 120 may receive imaging data or projection data from the CT detector 114. As one more example, the processing unit 120 may provide control signals to one or more aspects of the CT acquisition unit 110, such as the X-ray source 112 and CT detector 114. The processing unit 120 may include processing circuitry configured to perform one or more tasks, functions, or steps discussed herein. It may be noted that "processing unit" as used herein is not intended to necessarily be limited to a single processor or computer. For example, the processing unit 120 may include multiple processors and/or computers, which may be integrated in a common housing or unit, or which may distributed among various units or housings.

The depicted processing unit 120 is configured to control the CT acquisition unit (e.g., by controlling the time durations between blanking periods or intervals that define the duration length of an individual acquisition period or view) to vary the view duration during a series of views that are used in generating an image. In various embodiments, the series of views thus may include a first group of views having a first view duration and a second group of views having second view duration that is different than the first view duration. The view duration may be varied during a single rotation (or portion thereof) at a given position along a length of an object being imaged, and/or may be varied between rotations at different positions along the length of the object.

Figure 2:
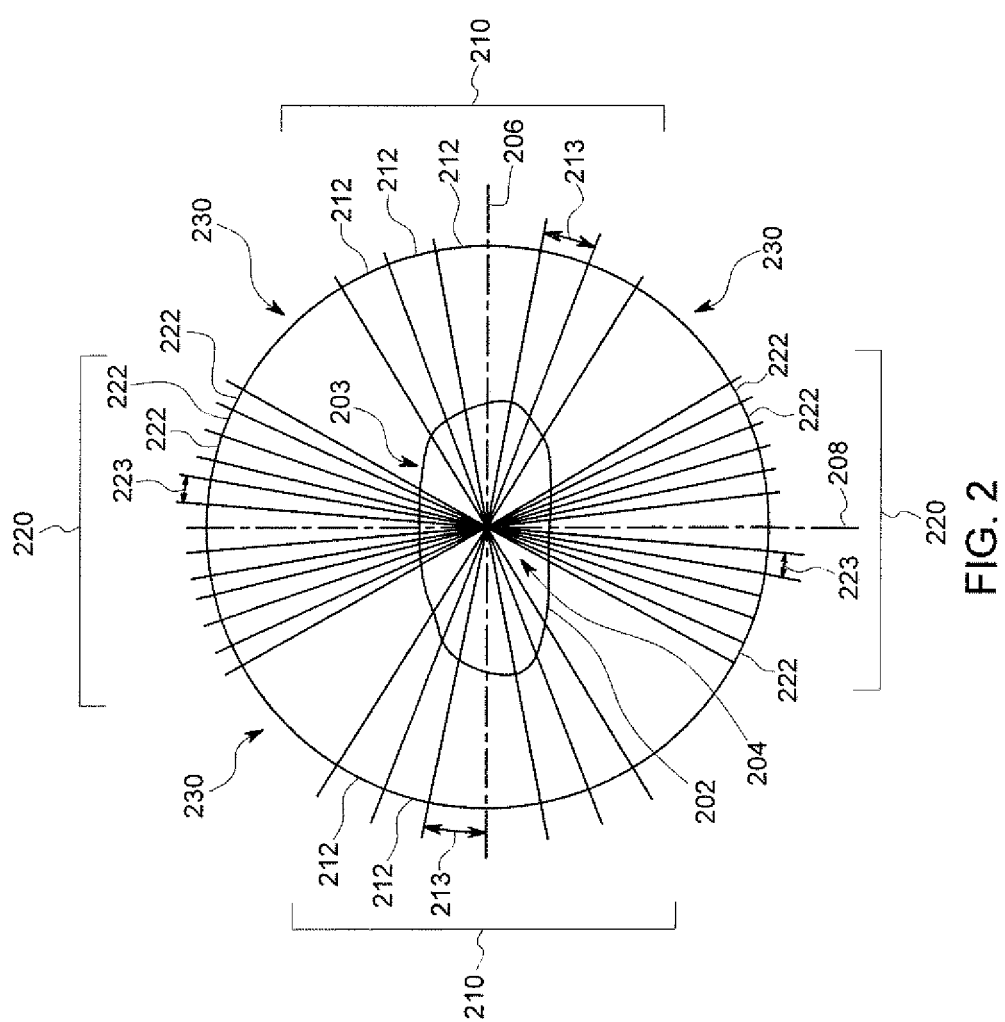
FIG. 2 illustrates different groups of views in a rotation in accordance with various embodiments.

FIG. 2 illustrates an example of different view lengths within a single rotation. In the example illustrated in FIG. 2, an object 202 to be imaged includes an oblong cross-sectional shape 203 that includes a long axis 206 and a short axis 208 that pass through an iso-center 204. The iso-center 204 also passes through the center of the bore of the gantry and is the point about which the X-ray source and CT detector rotate. In the illustrated embodiment, due to the variation in thickness of the object 202 as the view angle changes, the attenuation of the object 202 also changes with view angle. The attenuation of the depicted object 204 is greater along the long axis 206 than along the short axis 208. Thus, if the rotational speed and view duration are maintained constant throughout the rotation, a greater radiation flux (or counts, or imaging information) will be received at the views aligned along or close to the short axis 206. The attenuation along the long axis 206 may result in lower counts for views aligned along or close to the long axis 206, resulting in low IQ metrics (e.g., a low signal to noise ratio (SNR)) for those views, and noise may dominate the signal. Accordingly, in various embodiments, the view length or duration for views aligned along or near the long axis 206 may be increased to provide a longer period for radiation flux reception for those views, and improving SNR.

As seen in FIG. 2, a first group 210 of views 212 corresponds to (e.g., is positioned along or near) the long axis 206 for which the attenuation is greater, and a second group 220 of views 222 corresponds to (e.g., is positioned along or near) the short axis 208 for which the attenuation is less. The first group 210 is located at and around the far right and far left of FIG. 2 (or at positions corresponding to 3:00 and 9:00) and the second group 220 is located at and around the top and bottom of FIG. 2 (or at positions corresponding to 12:00 and 6:00), such that X-rays that have passed through the thickest (or most attenuating) portions of the object 202 are collected during the first group 210 of views 212, and X-rays that have passed through the thinnest (or least attenuating) portions of the object 202 are collected during the second group 220 of views 222. As seen in FIG. 2, the views 212 of the first group 210 have a first duration 213 that is longer than a second duration 223 of the views 222 of the second group 220. Thus, the processing unit 120 may control the CT acquisition unit 110 (e.g., by controlling the acquisition times for the CT detector 114) to have the first group 210 of views 212 have a longer duration to provide for additional time to collect CT imaging information during those views to address the increase in attenuation for those views. For example, the attenuation for various view angles may be determined based on a scout scan, with the processing unit 120 determining view durations for one or more groups of views based on the attenuation distribution across the various view angles. The precise number of views for a group of views may be determined based on a desired image quality, a distance of one more regions of interest from an iso-center (e.g., to minimize blurring), or the like. Further, additional groups that have views having different view durations may also be employed within a given rotation (or portion thereof). For example, a third group 230 of views (individual views not shown for clarity of illustration) may be provided disposed between the first group 210 and the second group 230, with the views of the third group 230 having an intermediate individual view duration that is larger than the second view duration 223 of the second group 220 but shorter than the first view duration 213 of the first group 210.

Figure 3:
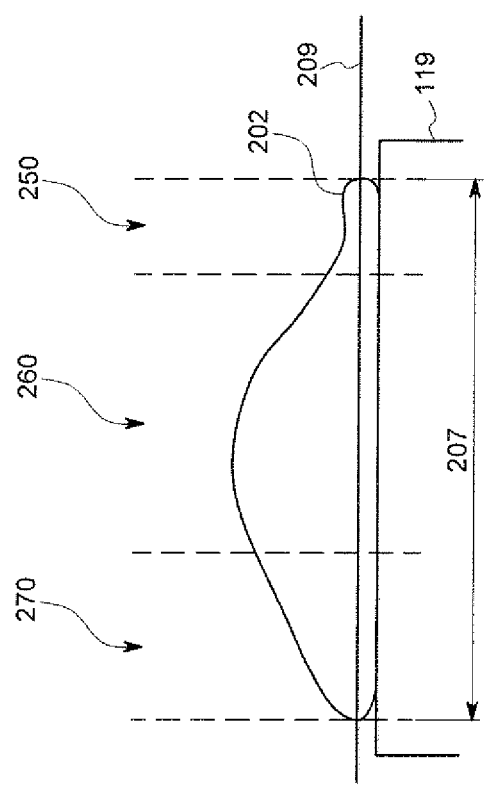
FIG. 3 illustrates different imaging locations along a length of an object in accordance with various embodiments.

As indicated above, the view duration may also be varied (e.g., under the control of the processing unit 120) for different rotations of the CT acquisition unit that take place at different positions along a length of an object. FIG. 3 illustrates an example of different positions along a length of an object for which view duration may be varied. FIG. 3 provides a side view of the object 202 that was shown in cross-section in FIG. 2, with the object 202 supported by a bed 119. As seen in FIG. 3, the object 202 includes a longitudinal axis 209 that extends transverse to the long axis 206 and the short axis 208 shown in FIG. 2. The overall length 207 of the object 202 may be longer than the aperture opening of the CT acquisition unit 110. Accordingly, the CT acquisition unit 110 may be rotated at a first position along the length 207 to acquire information for a first portion (or slab) of the object 202, then moved to a second position along the length 207 to acquire information for a second portion (or slab) of the object 202, and so on until the entire object 202 (or entire portion of the object 202 for which imaging information is desired) has been scanned. In FIG. 3, three positions are shown along the length 207 of the object 202: a first position 250, a second position 260, and a third position 270. Depending on, for example, the size and/or shape, the attenuation, and the desired image quality for a given position, the view duration may be varied for that position relative to the other longitudinal positions. For example, each of the first position 250, second position 260, and third position 270 may have a uniform view duration for a rotation at the given position, but the view duration for each position may be different than for the other positions. In some embodiments, the view duration may also be varied during a given rotation or at a given position. It may be noted that other arrangements may be employed in alternate embodiments. For example, a helical path may be employed for the CT acquisition unit 110, with the view duration varied during travel along the helical path.

Returning to FIG. 1, in the illustrated embodiment, the processing unit includes a reconstruction module 122, a determination module 124, a control module 126, and a memory 128. It may be noted that other types, numbers, or combinations of modules may be employed in alternate embodiments, and/or various aspects of modules described herein may be utilized in connection with different modules additionally or alternatively. Generally, the various aspects of the processing unit 120 act individually or cooperatively with other aspects to perform one or more aspects of the methods, steps, or processes discussed herein.

The depicted reconstruction module 122 is configured to reconstruct one or more images using imaging or projection data acquired from the CT detector 114 and/or imaging information from the PET acquisition unit 130. For example, the reconstruction module 122 may receive information from a scout scan (e.g., a low resolution image, or image taken only at one stationary view, or otherwise limited image) to reconstruct a scout image, from which the determination module 124 may determine a size and/or shape of an object and/or region of interest within the object to be used in determining the size and/or variation of duration lengths to be used in CT image acquisition. As another example, the reconstruction module 122 may receive imaging information from the CT detector taken over a number of views (e.g., for a full rotation or portion thereof, or for a number of rotations taken at different positions along the length of an object to be imaged) and reconstruct an image used for diagnostic purposes. As another example, the reconstruction module 122 may receive CT imaging information from the CT detector and PET information from the PET acquisition unit 130, use the information from the CT detector to perform attenuation correction on the PET information, and reconstruct an image using the attenuation corrected PET information.

In the illustrated embodiment, the determination module 124 is configured to receive information from the reconstruction module 122 (e.g., a scout scan or scout information) and/or the input unit 150 (e.g., information describing or corresponding to a patient, procedure, scanning parameters, desired image quality, system or system capabilities, among others) and to determine view duration for one or more series of views, whether the duration should be varied to achieve IQ goals, and/or how the view duration is to be varied. The determination module 124 may be communicably coupled to the control module 126, with the control module 126 configured to control the CT acquisition unit 110 and/or other aspects of the system 100 to implement the settings proscribed by the determination module 124. For example, a larger view duration (or lower number of views) may be employed where attenuation is higher. As another example, a larger view duration (or lower number of views) may be employed when a region of interest is disposed within a relatively close range of an iso-center or center of rotation of the CT acquisition unit 100. As one more example, a larger view duration (or lower number of views) may be utilized for tasks or applications where a lower dose is desired, such as for example a pediatric application, or, as another example, for attenuation correction in a PET/CT application where a lower image quality or resolution than desired for a CT diagnostic application may be acceptable. For example, image quality or resolution of PET images may be lower than image quality or resolution for CT images. The CT acquisition unit may be controlled (e.g., the radiation flux and view duration (or durations) controlled) to provide an image quality or resolution that corresponds to (e.g., matches or approximates) the PET image quality or resolution.

Again, the view duration may be varied during a rotation or for different rotations. For example, the determination unit 124 may determine a variation of view duration during a rotation to address changes in attenuation that change with view angle (e.g., provide a longer view duration for view angles having greater attenuation). As another example, the determination unit 124 may determine a variation of view duration during a rotation to address changes in the location of the region of interest with respect to an iso-center that change with view angle (e.g., provide a longer view duration for view angles for which the ROI has a shorter distance to the iso-center).

In some embodiments, the processing unit 120 (e.g., the determination module 124) is configured to determine a scan configuration. The scan configuration may specify one or more of radiation dose, scan setting parameters such as tube voltage and/or tube current, or scan speed, among others. The scan configuration may be determined, for example, according to predetermined or standard protocols, based on information from the input unit 150 (e.g., information describing the patient and/or procedure) and/or information form the reconstruction unit 122 (e.g., a scout scan from which patient size, shape, and/or attenuation may be determined). Next, the processing unit 120 (e.g., the determination module 124) may compare the scan configuration to a capability of the imaging system 100 (e.g., determine if the system 100 is capable of providing a radiation flux called for by the scan configuration). Alternatively or additionally, the processing unit (e.g., the determination module 124) may determine if a radiation flux called for by the scan configuration exceeds a prescribed dose limitation (e.g., a low dose limitation may be provided for pediatric applications, or for PET/CT applications where the CT information is only to be used for attenuation correction, among others). If the system 100 is not capable of providing the radiation flux called for by the scan configuration (or if the radiation flux called for by the scan configuration exceeds a prescribed dose limitation) the processing unit (e.g., the determination module 124) may then determine that view duration is to be varied, and to select a view duration modification that will provide a desired image quality while maintaining radiation flux within system capabilities and/or below a prescribed dose limitation. For example, a larger view duration may be employed for view angles corresponding to a thicker (or otherwise more attenuating) portion of a patient, to provide a longer acquisition time (or higher number of counts) and corresponding improved SNR for the thicker portions.

In some embodiments, the processing unit 120 (e.g., the determination module 124) is configured to identify a desired image quality (IQ). The IQ may be specified, for example, in terms of one or more IQ metrics, such as SNR. The desired IQ may be specified by a predetermined protocol or standard based on a diagnostic use or purpose of a CT image to be provided, for example. The view duration may then be varied to provide the desired IQ, while minimizing radiation dose. As one example, if a determined IQ provided by a scan setting provides an acceptable IQ or exceeds a desired IQ but uses a relatively high radiation dose or a dose higher than desired (e.g., a relatively low IQ such as may be required for attenuation correction for PET/CT imaging), the processing unit 120 may vary the view duration to provide a longer view duration to allow for lowering of the radiation dose while still providing acceptable IQ. As another example, if a desired IQ (e.g., SNR) is not met for all or a portion of rotation, the processing unit 120 may increase the view duration for that portion of the rotation to improve SNR while not increasing the radiation dose.

In some embodiments, the processing unit 120 may vary the radiation flux along with varying the view duration to provide even more flexibility in meeting radiation dose and/or IQ targets for objects that have varying attenuation for different view angles. For example, the radiation flux may be varied according to an automatic exposure control (AEC) scheme to provide additional radiation flux for high attenuation view angles relative to other view angles, while the view duration is varied to provide increased signal reception for the high attenuation view angles to further improve SNR for the high attenuation view angles and/or to reduce or minimize the additional radiation flux provided pursuant to the AEC technique.

In various embodiments, the processing unit 120 (e.g., the determination module 124) may also adjust view duration on based on a previously performed scan or portion of a scan. For example, if noise is higher than desired for a scan (or a portion thereof), the view duration may be increased for the scan (or portion thereof) to reduce the effect of noise (or increase SNR).

Thus, the determination module 124 may determine view duration (and/or one or more variations in view duration), for example, based on one or more of a thickness or attenuation of an object to be imaged, a radiation dose capability or limitation, and diagnostic requirements (e.g., IQ target) for a given protocol or procedure. The view duration may vary during rotation (e.g., to address changes in attenuation that change with view angle) or for different rotations (e.g., to address changes in attenuation that change along the length of an object being imaged). The determination module may specify and/or vary view duration to accomplish a desired IQ (e.g., noise metric). For example, by lengthening view duration more counts may be provided and SNR may be increased. Also, by lengthening view duration, SNR may be increased without increasing radiation dosage (e.g., when the radiation dose is at system capability limits, or at limits called for by a low-dose protocol). As one more example, by shortening duration, blurring may be reduced.

The control module 126 is configured, for example, to control the imaging system 100 to collect imaging information to be used in reconstructing an image. The control module 126, for example, may control the CT acquisition unit 110, to provide the view durations called for by the determination module 124. For example, the control module 126 may vary the timing interval between blanking periods of individual views or acquisition periods to provide varying view durations during a rotation being performed at a constant speed. (In theory, the rotational speed of the gantry 116 to which the X-ray source 112 and CT detector 114 are mounted may be varied additionally or alternatively to provide varying amounts of information collected during views or acquisition periods; however, variation of the rotational speed of the gantry during a single rotation may be difficult to achieve or control in practice, for example, due to the relatively large inertia of the various components.) The control module 126 may also control the X-ray source 112, for example, to provide a desired radiation flux for various portions of a rotation.

The output unit 140 is configured to provide information to the user. The output unit 140 may be configured to display, for example, a scout image or a final image. The output unit 140 may include one or more of a screen, a touchscreen, a printer, or the like.

The input unit 150 may be configured to obtain an input that corresponds to one or more settings or characteristics of a scan to be performed, and to provide the input (or information corresponding to the input) to the processing unit 120, which may use the input to determine, adjust, or select view durations for imaging information acquisition view durations, among others. The input may include, for example, a portion of the body to be scanned (e.g., head, body) and/or type of scan (e.g., pediatric, cardiac, or attenuation correction scan for PET/CT imaging, among others). The input unit 150 may be configured to accept a manual user input, such as via a touchscreen, keyboard, mouse, or the like. Additionally or alternatively, the input unit 150 may receive information from another aspect of the imaging system 100, another system, or a remote computer, for example, via a port or other connectivity device. The input unit 150 may also be configured to obtain user approval or denial of a proposed duration or durations, a corresponding radiation dosage, and/or a corresponding IQ metric (or metrics). As used herein, to "obtain" may include, for example, to receive.

Figure 4:
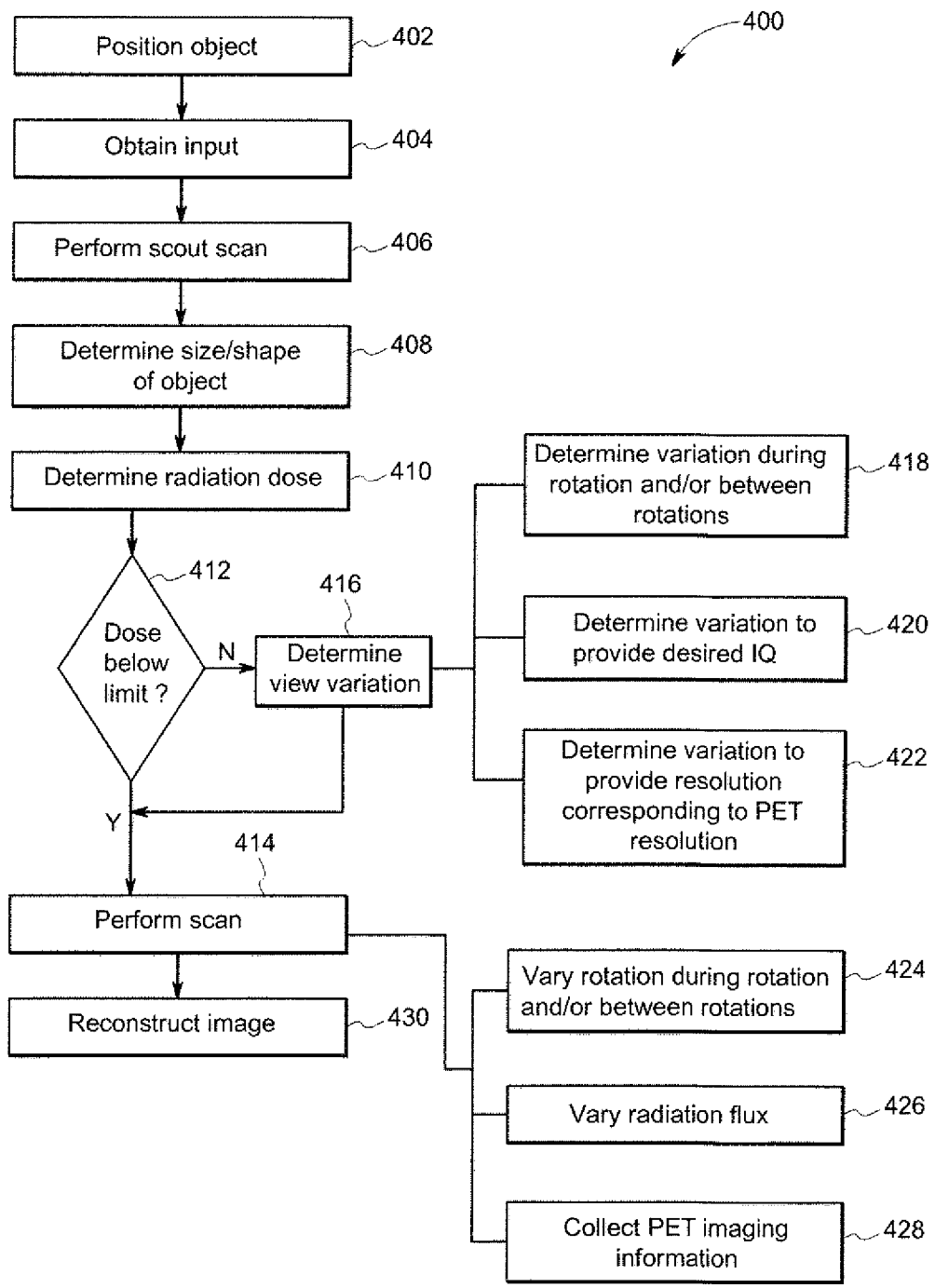
FIG. 4 is a flowchart of a method in accordance with various embodiments.

FIG. 4 provides a flowchart of a method 400 for imaging an object in accordance with various embodiments. The method 400, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 400 may be able to be used as one or more algorithms to direct hardware (e.g., one or more aspects of the processing unit 120) to perform one or more operations described herein.

At 402, an object to be imaged is positioned. For example, the object may be a human patient positioned on a table in a bore of a CT imaging system. As another example, the patient may be positioned within a bore of dual modality imaging system, such as a PET/CT system, or other system that combines CT with another imaging modality.

At 404, imaging input is obtained. For example, the imaging input may include a user input that includes a scan technique or scanning operational parameters (e.g., tube voltage, tube current, or the like). The input may also include an identification of a body portion (e.g., head, body), and/or information describing or corresponding to a scan protocol or diagnostic purpose for a resulting image (e.g., cardiac high-resolution scan, pediatric scan, or attenuation correction scan for PET/CT, among others). The input may be utilized for example, to set scanning parameters, including view duration or variation thereof.

At 406, a scout scan is performed. The scout scan may be performed with a limited radiation dose and/or at a limited number of views (or with the X-ray source and CT detector maintained at a stationary position).

At 408, the size and/or shape of the object (e.g., human patient) and/or region of interest of the object are determined. The scout scan may be used, for example, in connection with software configured to determine attenuation from the scout scan.

At 410, a radiation dose required to obtain a desired or prescribed image quality (IQ) is determined. For example, using the size and shape information determined using the scout scan, and using a predetermined IQ metric, various scanning parameters to achieve the desired IQ are determined. For example, X-ray tube voltage (kVp), X-ray tube current (mA), and scanning speed may be determined. The parameters may be determined based on calibrated and/or historical records of IQ's achieved for objects having similar sizes and/or shapes to the current object to be imaged. The desired IQ, for example, may be based on a standard or protocol corresponding to a diagnostic purpose or use for the image, based on information obtained or acquired at 404.

The determined radiation dose or flux is next compared to the capabilities of the imaging system and/or a patient- or procedure-specific radiation dose limit. At 412, if the system capability is sufficient to provide the determined dose or flux (and/or if the dose or flux does not exceed the patient- or procedure-specific dose limit), the method 400 may proceed to 414, and a scan may be performed using the scanning parameters determined at 410. Optionally, even if the system capabilities are sufficient and the dose limit not exceeded, the scan parameters may be modified. For example, if it is determined that the view duration may be increased without reduction in IQ (or with a reduction that will not meaningfully impact the diagnostic usefulness of the image produced), then the scan parameters may be modified to reduce dosage and increase view duration. If system capabilities are not sufficient to provide the flux prescribed at 410 (and/or if the dose exceeds a dose limitation, e.g., for a low dose protocol), the method 400 may proceed to 416. For example, system capabilities or radiation dose limits may be exceeded, especially in the case of large patients and/or low dose protocols.

At 416, a view variation is determined. Generally, the view variation in various embodiments provides for different lengths of view (or view number, or view frequency) during a rotation of a CT acquisition system (see, e.g., FIG. 2 and related discussion) and/or at different rotations for different longitudinal positions of an object (see, e.g., FIG. 3 and related discussion), as shown at 418. The view duration may be varied to provide a desired IQ, as shown at 420. For example, if system capabilities are not sufficient to provide a desired flux for a group of view angles of a rotation, the view duration for the views included in the group of view angles may be increased, to increase signal acquisition time for the views and thereby improving SNR. Generally, the closer a region of interest is to an iso-center of the system, the longer the view duration may be made without incurring significant blurring penalties. The view duration may also be varied to achieve the desired IQ while minimizing or reducing a radiation dose. For example, if it is determined that view duration may be increased while still providing a useful image, the view duration may be increased and the radiation dose decreased. The view duration may also be varied based on a diagnostic purpose, an example of which is shown at 422. For example, PET images typically have lower resolution than CT images. Consequently, CT images used only for PET attenuation correction may have lower resolution requirements. Accordingly, a view duration may be increased (and radiation dose decreased) so that CT imaging information acquired for PET attenuation correction may have an image quality or resolution corresponding to (e.g., matching or approximating) an expected or predetermined PET image quality or resolution.

At 414, a scan is performed. The X-ray source and detector may be rotated about the object being imaged and operated in a manner prescribed by predetermined scanning parameters to collect imaging information at the detector. Imaging or projection data or information is obtained via the detector during the performance of the scan. As indicated herein, the view duration (or period of image acquisition) may be varied (e.g., at a constant speed of gantry rotation) to provide improved flexibility or control over the amount of information or signals collected at each view (e.g., view duration may be increased to collect additional information or signals at view angles experiencing relatively higher levels of attenuation). For example, at 424, the view duration is varied for views of a rotation and/or for different rotations along the length of the object. Further, during performance of the scan, other scanning parameters may be varied during a rotation or between different rotations in conjunction with the variation in view duration. For example, at 426, the radiation flux provided from an X-ray source may be varied during a rotation or between different rotations. The X-ray flux may be varied in accordance with an AEC scheme or technique as discussed herein. For example, both X-ray flux and view duration may be increased for view angles having particularly high attenuation. In some embodiments, the scan may include collection of PET imaging information, as shown at 428.

At 430, an image is reconstructed (e.g., using reconstruction module 122 or other aspect of processing unit 120). The reconstruction image may be provided using the CT imaging information collected for all or a portion of the views or groups of views. For example, with reference to FIG. 2, CT imaging information from views of the first group 210, the second group 220, and the third group 230 may be used together to reconstruct a 3-dimensional CT image. In some embodiments, the image may be reconstructed using PET imaging information that has been attenuation corrected using CT imaging information.

Figure 5:
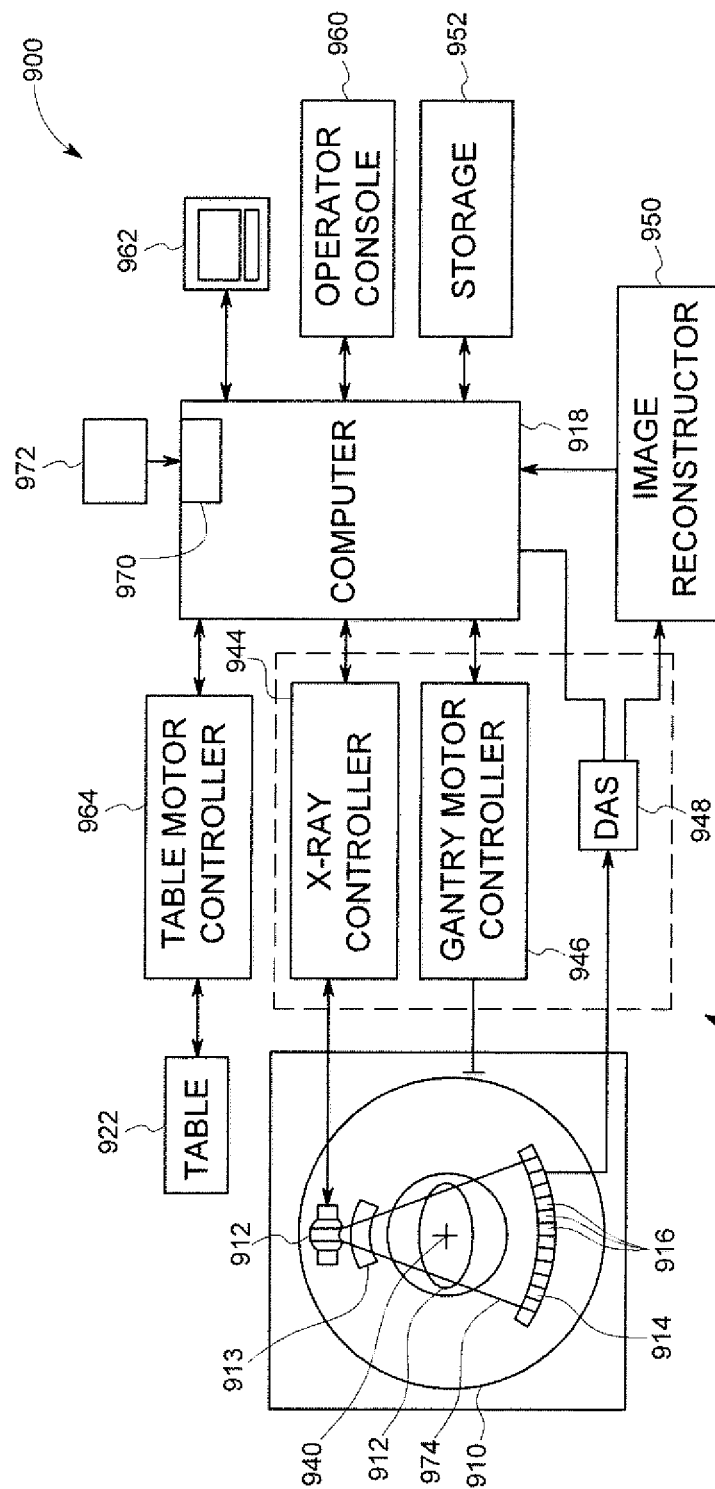
FIG. 5 is a schematic block diagram of an imaging system in accordance with various embodiments.

Various methods and/or systems (and/or aspects thereof) described herein may be implemented using a medical imaging system. For example, FIG. 5 is a block schematic diagram of an exemplary CT imaging system 900 that may be utilized to implement various embodiments discussed herein. Although the CT imaging system 900 is illustrated as a standalone imaging system, it should be noted that the CT imaging system 900 may form part of a multi-modality imaging system in some embodiments (see, e.g., FIGS. 6-7 and related discussion). For example, the multi-modality imaging system may include the CT imaging system 900 and a positron emission tomography (PET) imaging system, or a single photon emission computed tomography (SPECT) imaging system. It should also be understood that other imaging systems capable of performing the functions described herein are contemplated as being used.

The CT imaging system 900 includes a gantry 910 that has the X-ray source 912 that projects a beam of X-rays toward the detector array 914 on the opposite side of the gantry 910. A source collimator 913 and a bowtie filter module 915 are provided proximate the X-ray source 912. The detector array 914 includes a plurality of detector elements 916 that are arranged in rows and channels that together sense the projected X-rays that pass through a subject 917. The imaging system 900 also includes a computer 918 that receives the projection data from the detector array 914 and processes the projection data to reconstruct an image of the subject 917. The computer 918, for example, may include one or more aspects of the processing unit 120, or be operably coupled to one or more aspects of the processing unit 120. In operation, operator supplied commands and parameters are used by the computer 918 to provide control signals and information to reposition a motorized table 922. More specifically, the motorized table 922 is utilized to move the subject 917 into and out of the gantry 910. Particularly, the table 922 moves at least a portion of the subject 917 through a gantry opening (not shown) that extends through the gantry 910. Further, the table 922 may be used to move the subject 917 vertically within the bore of the gantry 910.

The depicted detector 914 includes a plurality of detector elements 916. Each detector element 916 produces an electrical signal, or output, that represents the intensity of an impinging X-ray beam and hence allows estimation of the attenuation of the beam as it passes through the subject 917. During a scan to acquire the X-ray projection data, the gantry 910 and the components mounted thereon rotate about a center of rotation 940. FIG. 5 shows only a single row of detector elements 916 (i.e., a detector row). However, the multislice detector array 914 includes a plurality of parallel detector rows of detector elements 916 such that projection data corresponding to a plurality of slices can be acquired simultaneously during a scan.

Rotation of the gantry 910 and the operation of the X-ray source 912 are governed by a control mechanism 942. The control mechanism 942 includes an X-ray controller 944 that provides power and timing signals to the X-ray source 912 and a gantry motor controller 946 that controls the rotational speed and position of the gantry 910. A data acquisition system (DAS) 948 in the control mechanism 942 samples analog data from detector elements 916 and converts the data to digital signals for subsequent processing. An image reconstructor 950 receives the sampled and digitized X-ray data from the DAS 948 and performs high-speed image reconstruction. The reconstructed images are input to the computer 918 that stores the image in a storage device 952. The computer 918 may also receive commands and scanning parameters from an operator via a console 960 that has a keyboard. An associated visual display unit 962 allows the operator to observe the reconstructed image and other data from computer. It may be noted that one or more of the computer 918, controllers, or the like may be incorporated as part of a processing unit such as the processing unit 160 discussed herein.

The operator supplied commands and parameters are used by the computer 918 to provide control signals and information to the DAS 948, the X-ray controller 944 and the gantry motor controller 946. In addition, the computer 918 operates a table motor controller 964 that controls the motorized table 922 to position the subject 917 in the gantry 910. Particularly, the table 922 moves at least a portion of the subject 917 through the gantry opening.

In various embodiments, the computer 918 includes a device 970, for example, a CD-ROM drive, DVD drive, magnetic optical disk (MOD) device, or any other digital device including a network connecting device such as an Ethernet device for reading instructions and/or data from a tangible non-transitory computer-readable medium 972, that excludes signals, such as a CD-ROM, a DVD or another digital source such as a network or the Internet, as well as yet to be developed digital means. In another embodiment, the computer 918 executes instructions stored in firmware (not shown). The computer 918 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the X-ray source 912 and the detector array 914 are rotated with the gantry 910 within the imaging plane and around the subject 917 to be imaged such that the angle at which an X-ray beam 974 intersects the subject 917 constantly changes. A group of X-ray attenuation measurements, i.e., projection data, from the detector array 914 at one gantry angle is referred to as a "view". A "scan" of the subject 917 comprises a set of views made at different gantry angles, or view angles, during one or more revolutions of the X-ray source 912 and the detector 914. In a CT scan, the projection data is processed to reconstruct an image that corresponds to a three-dimensional volume taken of the subject 917. It may be noted that, in some embodiments, an image may be reconstructed using less than a full revolution of data. For example, with a multi-source system, substantially less than a full rotation may be utilized. Thus, in some embodiments, a scan (or slab) corresponding to a 360 degree view may be obtained using less than a complete revolution.

Figure 6:
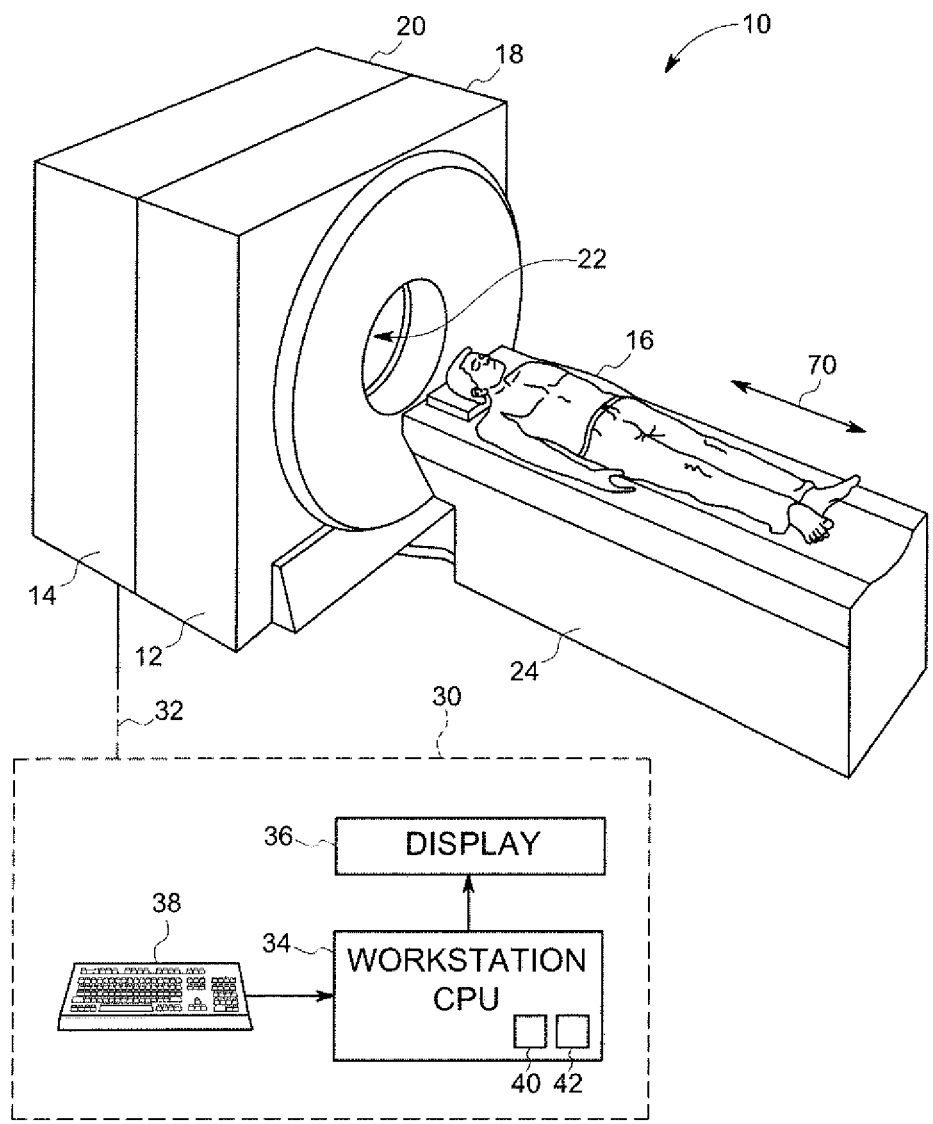
FIG. 6 is a schematic block diagram of an imaging system in accordance with various embodiments.

Various methods and/or systems (and/or aspects thereof) described herein may be implemented using a multi-modality medical imaging system, such as the imaging system 10 shown in FIG. 6. In various embodiments, the imaging system 10 is a multi-modality imaging system that includes different types of medical imaging systems, such as a Positron Emission Tomography (PET), a Single Photon Emission Computed Tomography (SPECT), a Computed Tomography (CT), an ultrasound system, a Magnetic Resonance Imaging (MRI) or any other system capable of generating diagnostic images. In the illustrated embodiment, the imaging system 10 is a PET/CT system. It may be noted that various embodiments are not necessarily limited to medical imaging systems for imaging human subjects, but may include veterinary or non-medical systems for imaging non-human objects, etc.

Referring to FIG. 6, the multi-modality imaging system 10 includes a first modality unit 12 and a second modality unit 14. The two modality units enable the multi-modality imaging system 10 to scan an object or subject 16 in a first modality using the first modality unit 12 and to scan the subject 16 in a second modality using the second modality unit 14. The multi-modality imaging system 10 allows for multiple scans in different modalities to facilitate an increased diagnostic capability over single modality systems. In the illustrated embodiment, the first modality 12 is a PET imaging system and the second modality 14 is a CT system. The imaging system 10 is shown as including a gantry 18 that is associated with the PET imaging system 12 and a gantry 20 that is associated with the CT system 14. During operation, the subject 16 is positioned within a central opening 22, defined through the imaging system 10, using, for example, a motorized table 24.

The imaging system 10 also includes an operator workstation 30. During operation, the motorized table 24 moves the subject 16 into the central opening 22 of the gantry 18 and/or 20 in response to one or more commands received from the operator workstation 30. The workstation 30 then operates the first and/or second modalities 12 and 14 to both scan the subject 16 and to acquire PET emission data 40 and/or CT data 42 of the subject 16. The workstation 30 may be embodied as a personal computer (PC) that is positioned near the imaging system 10 and hard-wired to the imaging system 10 via a communication link 32. The workstation 30 may also be embodied as a portable computer such as a laptop computer or a hand-held computer that transmits information to, and receives information from the imaging system 10. Optionally, the communication link 32 may be a wireless communication link that enables information to be transmitted to and/or from the workstation 30 to the imaging system 10 wirelessly. In operation, the workstation 30 is configured to control the operation of the imaging system 10 in real-time. The workstation 30 is also programmed to perform medical image diagnostic acquisition and reconstruction processes described herein.

The operator workstation 30 includes a central processing unit (CPU) or computer 34, a display 36, and an input device 38. As used herein, the term "computer" may include any processor-based or microprocessor-based system including systems using microcontrollers, reduced instruction set computers (RISC), application specific integrated circuits (ASICs), field programmable gate array (FPGAs), logic circuits, and any other circuit or processor capable of executing the functions described herein. The above examples are exemplary only, and are thus not intended to limit in any way the definition and/or meaning of the term "computer". In the exemplary embodiment, the computer 34 executes a set of instructions that are stored in one or more storage elements or memories, in order to process information received from the first and second modalities 12 and 14. The storage elements may also store data or other information as desired or needed. The storage element may be in the form of an information source or a physical memory element located within the computer 34.

The set of instructions may include various commands that instruct the computer 34 as a processing machine to perform specific operations such as the methods and processes of the various embodiments described herein. The set of instructions may be in the form of a software program or the non-transitory computer readable medium. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Figure 7:
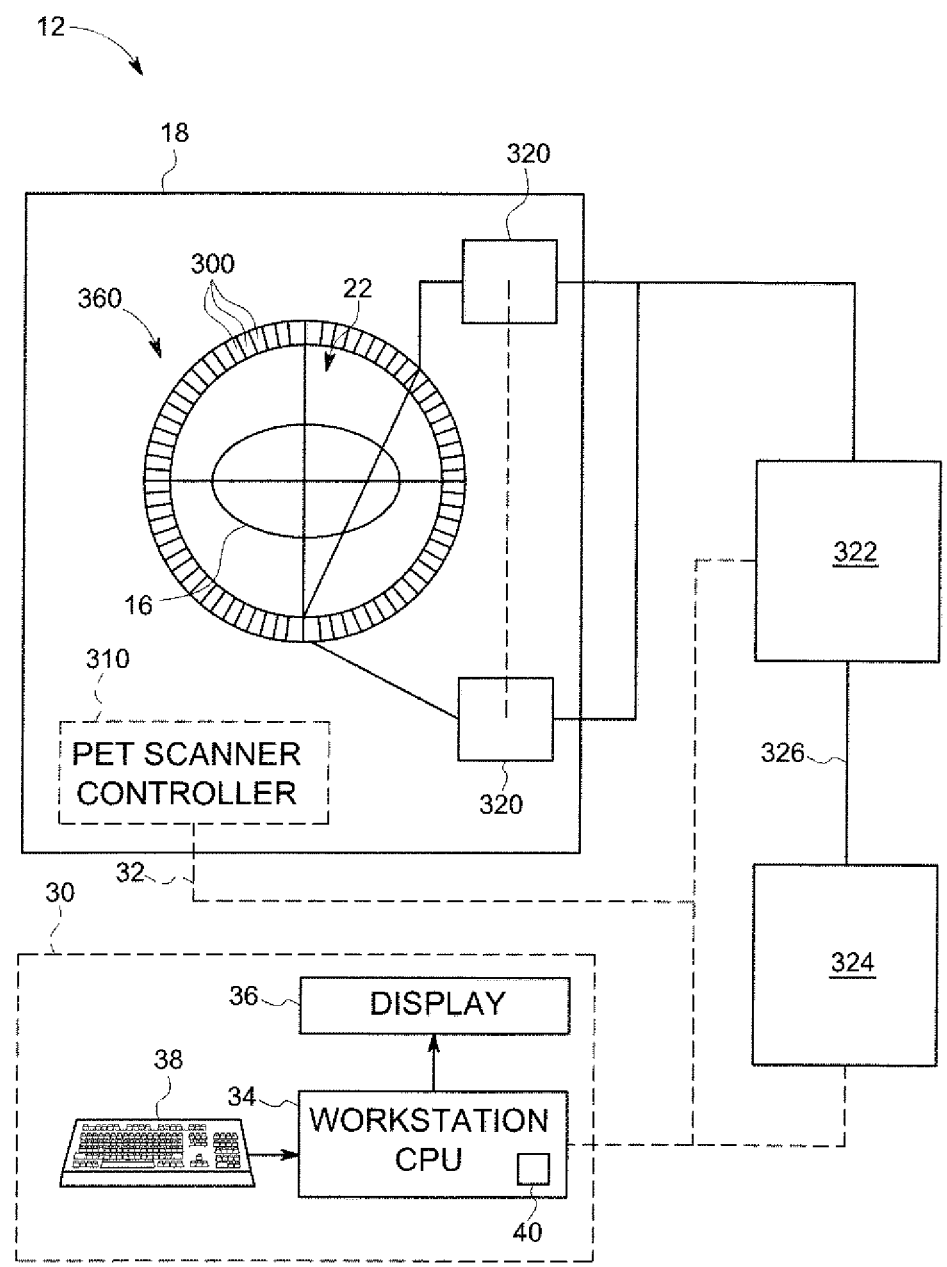
FIG. 7 is a schematic block diagram of an imaging system in accordance with various embodiments.

FIG. 7 is a block schematic diagram of the second modality unit 12, e.g. the PET imaging system, shown in FIG. 6. As shown in FIG. 6, the PET system 12 includes a detector array 360 that is arranged as ring assembly of individual detector modules 300. The detector array 360 also includes the central opening 22, in which an object, such as the subject 16 may be positioned, using, for example, the motorized table 24 (shown in FIG. 6). The motorized table 24 is aligned with the central axis of the detector array 360. During operation, the motorized table 24 moves the subject 16 into the central opening 22 of the detector array 360 in response to one or more commands received from the operator workstation 30. More specifically, a PET scanner controller 310 responds to the commands received from the operator workstation 30 through the communication link 32. Therefore, the scanning operation is controlled from the operator workstation 30 through PET scanner controller 310.

During operation, when a photon collides with a scintillator on the detector array 360, the photon collision produces a scintilla on the scintillator. The scintillator produces an analog signal that is transmitted to an electronics section (not shown) that may form part of the detector array 360. The electronics section outputs an analog signal when a scintillation event occurs. A set of acquisition circuits 320 is provided to receive these analog signals. The acquisition circuits 320 process the analog signals to identify each valid event and provide a set of digital numbers or values indicative of the identified event. For example, this information indicates when the event took place and the position of the scintillation scintillator that detected the event.

The digital signals are transmitted through a communication link, for example, a cable, to a data acquisition controller 322. The data acquisition processor 322 is adapted to perform the scatter correction and/or various other operations based on the received signals. The PET system 12 may also include an image reconstruction processor 324 that is interconnected via a communication link 326 to the data acquisition controller 322. During operation, the image reconstruction processor 324 performs various image enhancing techniques on the digital signals and generates an image of the subject 16.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. An imaging system comprising:
a computed tomography (CT) acquisition unit comprising an X-ray source and a CT detector configured to collect CT imaging data of an object to be imaged, the X-ray source and CT detector configured to be rotated about the object to be imaged and to collect a series of views of the object as the X-ray source and CT detector rotate about the object to be imaged; and
a processing unit operably coupled to the CT acquisition unit and configured to control the CT acquisition unit to vary a view duration for the views of the series, the view duration for a particular view defining an angular range of rotation between blanking periods separating the particular view from adjacent views for an imaging information acquisition period for the particular view, wherein the angular range of rotation varies with variation of the view duration, wherein the series of views includes a first group of views having a first view duration and a second group of views having a second view duration that is different than the first view duration.

2. The imaging system of claim 1, wherein the processing unit is further configured to vary the view duration based on a variation in attenuation of the object to be imaged, wherein the object has a first attenuation along a first axis and a second attenuation that is less than the first attenuation along a second axis, wherein the first group of views has a longer duration than the second group of views and corresponds to the first axis, and wherein the second group of views has a shorter duration than the first group of views and corresponds to the second axis.

3. The imaging system of claim 1, wherein the first group of views is collected for a first position located along a length of the object and the second group of views is collected for a second position that is different than the first position located along the length of the object.

4. The imaging system of claim 1, wherein the processing unit is configured to identify a desired image quality (IQ) and to vary the view duration based on the identified IQ to achieve the desired IQ and minimize radiation dose.

5. The imaging system of claim 1, further comprising a positron emission tomography (PET) acquisition unit, wherein the imaging system is configured to use imaging information obtained via the CT acquisition unit for attenuation correction, and wherein the processing unit is configured to vary the view duration to provide an image quality corresponding to an image quality provided by the PET acquisition unit.

6. The imaging system of claim 1, wherein the processing unit is configured to determine a scan configuration including a desired radiation dose to be provided by the CT acquisition unit to achieve a desired IQ at a uniform view duration, compare the determined scan configuration to a capability of the imaging system to provide the desired radiation dose, and, if the capability of the imaging system does not meet the determined scan configuration, to vary the view duration to provide the desired IQ.

7. The imaging system of claim 1, wherein the processing unit is further configured to control the X-ray source to provide a first radiation flux for the first group of views and a second radiation flux that is different than the first radiation flux for the second group of views.

8. A method comprising:
acquiring computed tomography (CT) imaging data of an object using a CT acquisition unit comprising an X-ray source and CT detector that rotate about the object, wherein the CT imaging data is acquired in a series of views as the X-ray source and CT detector are rotated about the object;

controlling the CT acquisition unit, during CT imaging data acquisition, to vary a view duration for the views of the series, the view duration for a particular view defining an angular range of rotation between blanking periods separating the particular view from adjacent views for an imaging information acquisition period for the particular view, wherein the angular range of rotation varies with variation of the view duration, wherein the series of views includes a first group of views having a first view duration and a second group of views having a second view duration that is different than the first view duration; and reconstructing an image using the CT imaging data.

9. The method of claim 8, wherein the object has a first attenuation along a first axis and a second attenuation that is less than the first attenuation along a second axis, wherein:
acquiring the CT imaging data for the first group of views comprises using a longer duration than for the second group of views, the first group of views corresponding with the first axis; and
acquiring the CT imaging data for the second group of views comprises using a shorter duration than for the first group of views, the second group of views corresponding with the second axis.

10. The method of claim 8, wherein:
acquiring the CT imaging data for the first group of views comprises collecting the first group of views at a first position located along a length of the object; and
acquiring the CT imaging data for the second group of views comprises collecting the second group of views at a second position located along the length of the object that is different from the first position.

11. The method of claim 8, further comprising:
determining a desired image quality (IQ); and
varying the view duration based on the identified IQ to achieve the desired IQ and minimize radiation dose.

12. The method of claim 8, further comprising:
acquiring positron emission tomography (PET) imaging information; and
varying the view duration to provide an image quality corresponding to an image quality of the PET imaging information;
wherein reconstructing the image comprises using the CT imaging data for attenuation correction of the PET imaging information.

13. The method of claim 8, further comprising:
determining a scan configuration to be provided by the CT acquisition unit to achieve a desired IQ at a uniform view duration, the scan configuration including a desired radiation dose;
comparing the determined scan configuration to a capability of the CT acquisition unit to provide the desired radiation dose; and,
if the capability of the imaging system does not meet the determined scan configuration, varying the view duration to provide the desired IQ.

14. The method of claim 8, further comprising controlling the X-ray source to provide a first radiation flux for the first group of views and a second radiation flux that is different than the first radiation flux for the second group of views.

15. A method comprising:
acquiring a scout image of an object using a computed tomography (CT) acquisition unit comprising an X-ray source and CT detector;

determining, using at least one processing unit, based on the scout image, a scan configuration to be provided by the CT acquisition unit to achieve a desired IQ at a uniform view duration, the scan configuration including a desired radiation dose;

comparing the determined scan configuration to a capability of the CT acquisition unit to provide the desired radiation dose;

and, if the capability of the imaging system does not meet the determined scan configuration, varying a view duration of views of a series during acquisition of CT imaging data to provide the desired IQ, the view duration for a particular view defining an angular range of rotation between blanking periods separating the particular view from adjacent views for an imaging information acquisition period for the particular view, wherein the angular range of rotation varies with variation of the view duration, wherein, during acquisition of CT imaging data, the X-ray source and CT detector are rotated about the object, wherein the CT imaging data is acquired in the series of views as the X-ray source and CT detector are rotated about the object; and reconstructing an image using the CT imaging data.

16. The method of claim 15, wherein varying the view duration comprises controlling the CT acquisition unit, during CT imaging data acquisition, to provide a first group of views having a first view duration and a second group of views having a second view duration that is different than the first view duration.

17. The method of claim 16, wherein the object has a first attenuation along a first axis and a second attenuation that is less than the first attenuation along a second axis, wherein:
acquiring the CT imaging data for the first group of views comprises using a longer duration than for the second group of views, the first group of views corresponding with the first axis; and
acquiring the CT imaging data for the second group of views comprises using a shorter duration than for the first group of views, the second group of views corresponding with the second axis.

18. The method of claim 16, wherein:
acquiring the CT imaging data for the first group of views comprises collecting the first group of views at a first position located along a length of the object; and
acquiring the CT imaging data for the second group of views comprises collecting the second group of views at a second position located along the length of the object that is different from the first position.

19. The method of claim 15, wherein the view duration is varied based on a size of a region of interest (ROI) of the object.

20. The method of claim 15, further comprising controlling the X-ray source to provide a first radiation flux for the first group of views and a second radiation flux that is different than the first radiation flux for the second group of views.

21. The imaging system of claim 1, wherein the processing unit is configured to determine the first view duration and the second view duration based on prior knowledge of the object.

22. The imaging system of claim 21, wherein the processing unit is configured to determine the first view duration and the second view duration based on a corresponding distance from the object to an iso-center of the imaging system.

* * * * *